US008822445B2

(12) United States Patent
Huang et al.

(10) Patent No.: US 8,822,445 B2
(45) Date of Patent: Sep. 2, 2014

(54) CRYSTALLINE FORM OF CARBAPENEM DERIVATIVE OR ITS HYDRATES AND PREPARATION METHODS AND USES THEREOF

(75) Inventors: Zhenhua Huang, Jinan (CN); Yanyan Dong, Jinan (CN)

(73) Assignee: Xuanzhu Pharma Co., Ltd., Jinan, Shandong Province (CN)

( * ) Notice: Subject to any disclaimer, the term of this patent is extended or adjusted under 35 U.S.C. 154(b) by 0 days.

(21) Appl. No.: 13/701,704

(22) PCT Filed: Jun. 1, 2011

(86) PCT No.: PCT/CN2011/000925
§ 371 (c)(1),
(2), (4) Date: Dec. 17, 2012

(87) PCT Pub. No.: WO2011/150679
PCT Pub. Date: Dec. 8, 2011

(65) Prior Publication Data
US 2013/0090325 A1 Apr. 11, 2013

(30) Foreign Application Priority Data

Jun. 3, 2010 (CN) .......................... 2010 1 0190636
Apr. 25, 2011 (CN) .......................... 2011 1 0104082

(51) Int. Cl.
*A61K 31/397* (2006.01)
*C07D 477/20* (2006.01)
*A61K 31/407* (2006.01)

(52) U.S. Cl.
CPC ............ *C07D 477/20* (2013.01); *A61K 31/407* (2013.01)
USPC ...................................... 514/210.13; 540/350

(58) Field of Classification Search
CPC . C07D 477/20; A61K 31/397; C07B 2200/13
USPC .......................... 540/350; 514/210.04, 210.13
See application file for complete search history.

(56) References Cited

U.S. PATENT DOCUMENTS

| 7,071,330 | B2 | 7/2006 | Williams et al. |
| 8,318,716 | B2 * | 11/2012 | Huang et al. ............. 514/210.13 |
| 2003/0153191 | A1 | 8/2003 | Saitoh et al. |
| 2004/0063931 | A1 | 4/2004 | William et al. |
| 2007/0060562 | A1 | 3/2007 | Saitoh et al. |
| 2008/0207586 | A1 | 8/2008 | Saitoh et al. |
| 2010/0197653 | A1 | 8/2010 | Huang et al. |
| 2011/0160177 | A1 | 6/2011 | Huang et al. |
| 2013/0079322 | A1 * | 3/2013 | Huang et al. ............. 514/210.13 |

FOREIGN PATENT DOCUMENTS

| CN | 1432016 A | 7/2003 |
| CN | 1486318 A | 3/2004 |
| CN | 101372489 A | 2/2009 |
| CN | 102250095 A | 11/2011 |
| EP | 1270575 A1 | 1/2003 |
| WO | WO-02057266 A1 | 7/2002 |

OTHER PUBLICATIONS

Mayo Clinic. Diseases and Conditions: Infectious Diseases. Jan. 23, 2013.*
International Search Report for International Application No. PCT/CN2011/000925, completed Jul. 15, 2011, mailed Sep. 8, 2011 (6 pages).
International Preliminary Report on Patentability for International Application No. PCT/CN2011/000925, issued Dec. 4, 2012 (5 pages).
Written Opinion for the International Searching Authority for International Application No. PCT/CN2011/000925, completed Aug. 30, 2011, mailed Sep. 8, 2011 (4 pages).

* cited by examiner

*Primary Examiner* — Golam M M Shameem
*Assistant Examiner* — Laura Daniel
(74) *Attorney, Agent, or Firm* — Clark & Elbing LLP

(57) ABSTRACT

The present invention relates to the crystalline form of carbapenems derivative or hydrate thereof and the preparation methods thereof. Specifically, the present invention relates to the crystalline form of carbapenem derivative (4R,5S,6S)-6-((R)-1-hydroxyethyl)-4-methyl-7-oxo-3-(((3S,5S)-5-((4-sulfamoylbenzyl)carbamoyl)pyrrolidin-3-yl)thio)-1-azabicyclo[3.2.0]hept-2-ene-2-carboxylic acid as represented by formula (I) or hydrate thereof, characterized in that the X-ray powder diffraction pattern thereof using Cu-Ka radiation represented as 2θ has characteristic peaks at 18.9±0.2, 19.4±0.2, 21.0±0.2, 21.7±0.2, and 23.4±0.2, the preparation methods thereof, and the use thereof in the preparation of medicament for treating and/or preventing infectious diseases, as well as a pharmaceutical composition comprising such compound and one or more pharmaceutical carriers and/or diluents.

20 Claims, 4 Drawing Sheets

Formula (I)

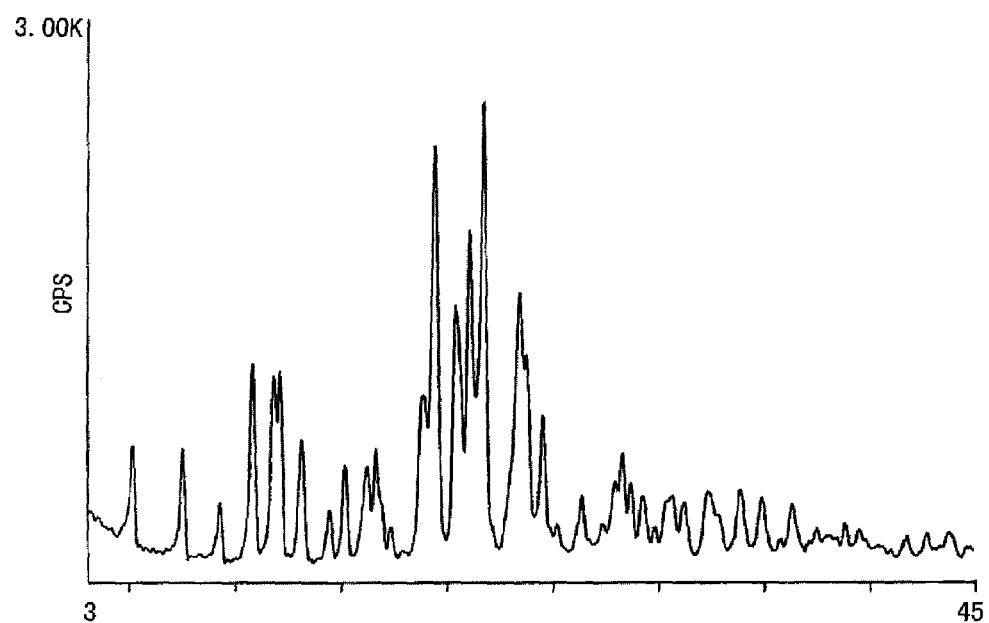
Figure 1. The X-ray powder diffraction pattern of the crystalline form II of compound A

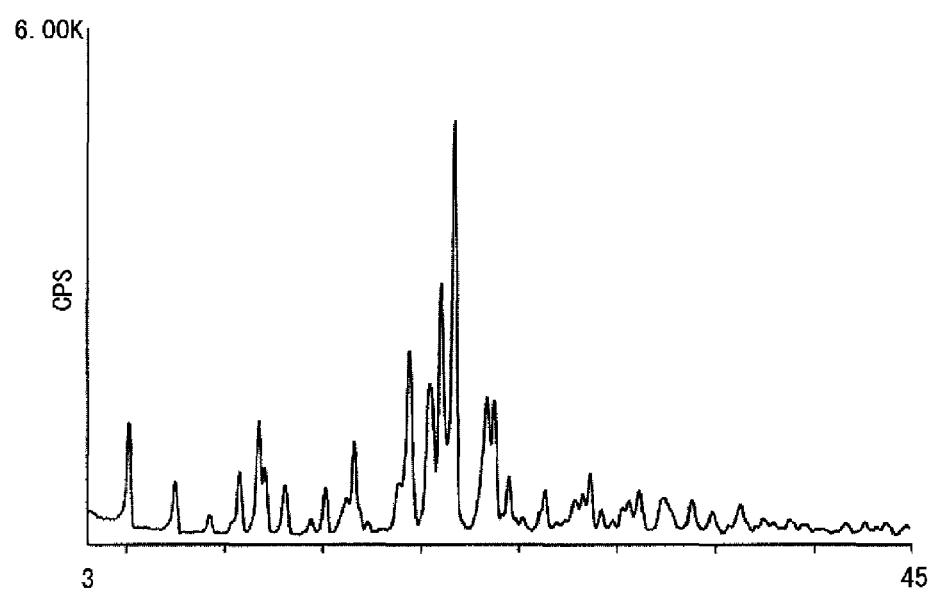
Figure 2. The X-ray powder diffraction pattern of the crystalline form II of compound A

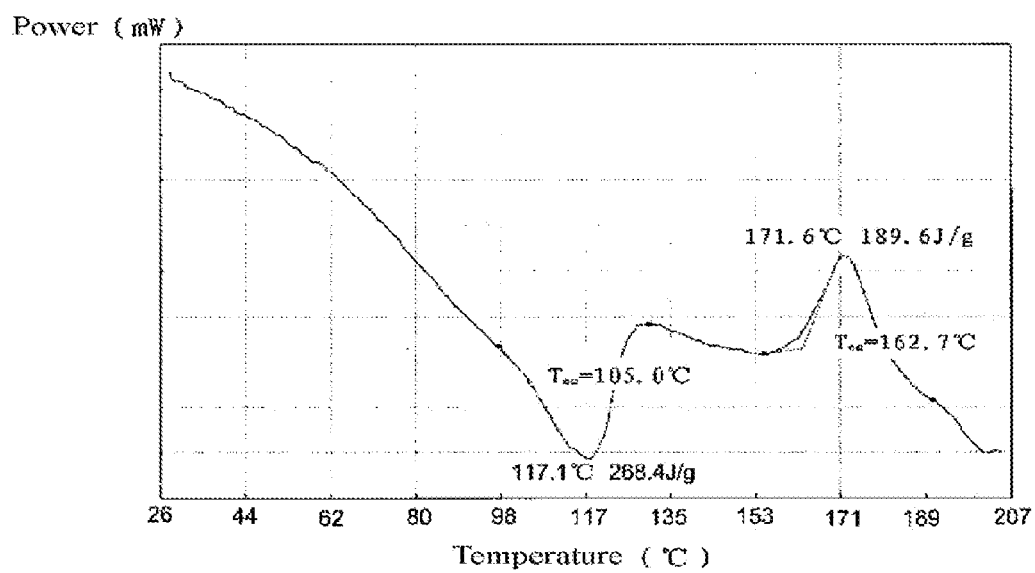
Figure 3. The DSC pattern of the crystalline form II of compound A

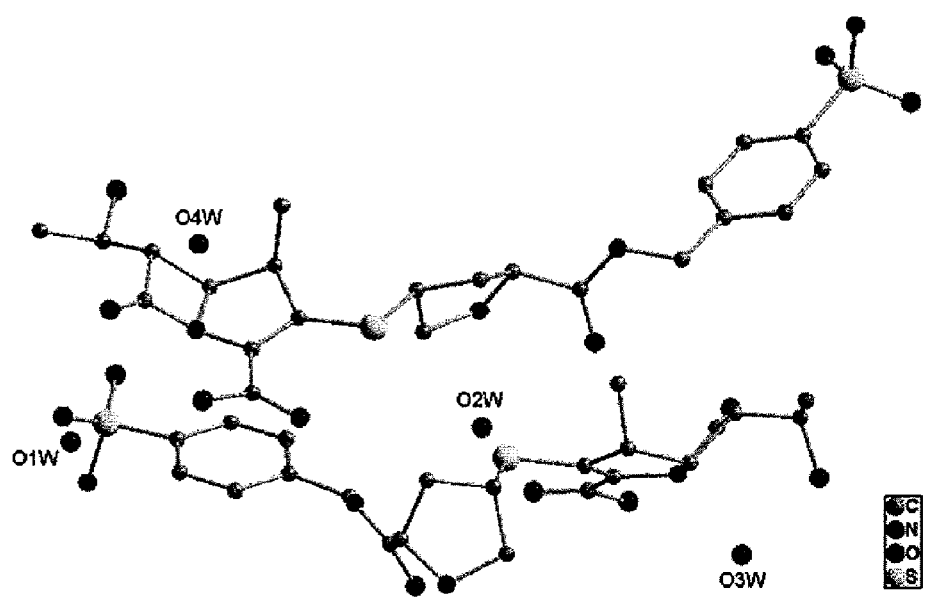
Figure 4. The molecular structure pattern as obtained by the single crystal diffraction of the crystalline form II of compound A

CRYSTALLINE FORM OF CARBAPENEM DERIVATIVE OR ITS HYDRATES AND PREPARATION METHODS AND USES THEREOF

CROSS-REFERENCE TO RELATED APPLICATIONS

This application is the U.S. National Stage filing under 35 U.S.C. §371 of International Application No. PCT/CN2001/000925, filed Jun. 1, 2001, which claims the benefit of Chinese Patent Application No. 201010190636.9, filed Jun. 3, 2010, and Chinese Patent Application No. 201110104082.0, filed Apr. 25, 2011.

TECHNICAL FIELD

The present invention relates to the field of medical technology. Specifically, the present application relates to the crystalline form of the carbapenems derivative (4R,5S,6S)-6-((R)-1-hydroxyethyl)-4-methyl-7-oxo-3-(((3S,5S)-5-((4-sulfamoylbenzyl)carbamoyl)pyrrolidin-3-yl)thio)-1-azabicyclo[3.2.0]hept-2-ene-2-carboxylic acid or hydrate thereof and preparation methods thereof, and use thereof in the preparation of a medicament for treating and/or preventing infectious diseases as well as a pharmaceutical composition comprising such compound and one or more pharmaceutical carriers and/or diluents.

BACKGROUND

Carbapenems antibiotics are novel β-lactam antibiotics that are developed initially from 1970s of the 20$^{th}$ century. Carbapenems are becoming more and more predominant in clinical use due to its extremely broad spectrum, superiorly high potency, resistance to enzymes and the like. Currently, the carbapenem antibiotics available on the market are imipenem-cilastatin, panipenem-betamipron, meropenem, ertapenem sodium, biapenem and doripenem.

The carbapenems derivative (4R,5S,6S)-6-((R)-1-hydroxyethyl)-4-methyl-7-oxo-3-(((3S,5S)-5-((4-sulfamoylbenzyl)carbamoyl)pyrrolidin-3-yl)thio)-1-azabicyclo[3.2.0]hept-2-ene-2-carboxylic acid as represented by formula (I) (refers to compound A for short in the Description, which has been described in CN200810127480.2) produces bactericidal action mainly by binding with penicillin binding protein (PBPs) in the bacterial cell membrane and inhibiting the synthesis of bacterial cell wall, which has preferable bactericidal action against both Gram-positive and Gram-negative bacteria.

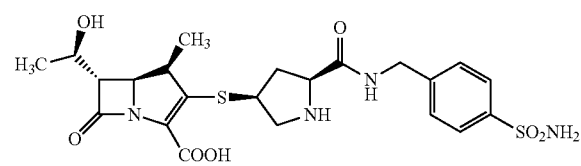

(I)

The study on crystalline form is very important in pharmaceutical development. Different crystalline forms of a compound have different properties. For example, different crystalline forms of a medicament have different stability, operation performance, solubility, and the like. Accordingly, the present inventors have conducted a number of studies on the crystalline forms of compound A, and thus identified and invented the crystalline forms of compound A.

The crystalline form I of compound A has been described in CN201010178970.2 in detail, and has characteristic peaks at 10.3±0.2, 14.5±0.2, 16.3±0.2, 17.1±0.2, 18.0±0.2, 20.8±0.2, 21.3±0.2, 22.0±0.2, and 23.3±0.2. Although the crystalline form I of compound A improves the stability of compound A to some extent, there is still a need to further improve and increase the stability and operation performance of compound A.

SUMMARY OF THE INVENTION

The object of the invention is to solve the problems as mentioned above by providing a novel crystalline form of compound A with better stability, better operability and superior solubility, as well as preparation methods and use thereof.

One object of the invention is to provide the crystalline form of compound A as represented by formula (I) or hydrate thereof, i.e. the crystalline form of carbapenem derivative (4R,5S,6S)-6-((R)-1-hydroxyethyl)-4-methyl-7-oxo-3-(((3S,5S)-5-((4-sulfamoylbenzyl)carbamoyl)pyrrolidin-3-yl)thio)-1-azabicyclo[3.2.0]hept-2-ene-2-carboxylic acid as represented by formula (I) or hydrate thereof, characterized in that the X-ray powder diffraction pattern thereof using Cu-Ka radiation represented as 2θ has characteristic peaks at 18.9±0.2, 19.4±0.2, 21.0±0.2, 21.7±0.2, and 23.4±0.2, Formula (I)

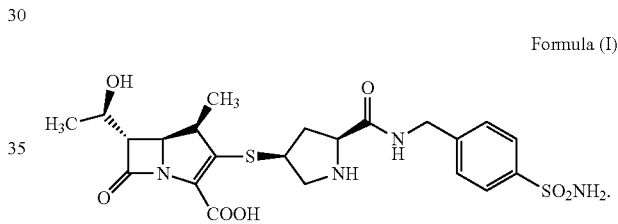

The X-ray powder diffraction pattern using Cu-Ka radiation represented as 2θ of said crystalline form of compound A or hydrate thereof has further characteristic peaks at 10.8±0.2, 11.8±0.2, 12.0±0.2, and 23.7±0.2 in addition to the aforementioned characteristic peaks.

The DSC endothermic transition of said crystalline form of compound A or hydrate thereof is at 105-117° C., and the highest decomposition temperature of said crystalline form of compound A or hydrate thereof is about 170-179° C.

The water content of said crystalline form of compound A or hydrate thereof is 6%-10%.

The present inventors have conducted a number of studies on the preparation methods of crystalline form of compound A or hydrate thereof. Since the molecular structure of compound A decides that compound A is an amphoteric substance that is both acidic and basic, this compound can be dissolved in both acidic and basic environments. The present invention also provides the preparation methods of the crystalline form of compound A or hydrate thereof.

The crystalline form of compound A (refers to the crystalline form II for short hereinafter) can be obtained by the following four methods.

Method 1

After adding bases or basic solutions to an aqueous suspension of compound A reach a homogeneous solution, adjusting pH to 5.4-7.0 with acids or acidic solutions, cooling to low temperature, filtering and drying to obtain a crystal.

Method 2

After adding acids or acid solutions to an aqueous suspension of compound A to reach a homogeneous solution, adjusting pH to 5.4-7.0 with bases or basic solutions, cooling to low temperature, filtering and drying to obtain a crystal.

Method 3

Formulating compound A as an aqueous suspension; after adjusting pH to reach a homogeneous solution, absorbing and enriching the solution by column chromatography, then eluting with an eluant of organic solvent/water; distilling the eluant off under reduced pressure to obtain a concentrated mixed solvent of organic solvent/water; adjusting pH to 5.4-7.0, cooling to low temperature, filtering and drying to obtain a crystal.

Method 4

Formulating compound A as an aqueous suspension; after adjusting pH to reach a homogeneous solution, adding a mixed solvent of organic solvent/water; adjusting pH to 5.4-7.0, cooling to low temperature, filtering and drying to obtain a crystal.

Said pH adjustment is adjusting pH with acids, acid solutions, bases or basic solutions. If pH is adjusted with acids or acid solutions prior to elution, pH is adjusted with bases or basic solutions after elution; if pH is adjusted with bases or basic solutions prior to elution, pH is adjusted with acids or acid solutions after elution.

In the step of adjusting pH with acids or acidic solutions as described in the aforementioned preparation methods 1-4, said acids are inorganic or organic acids, and said acidic solutions are solutions as formulated by dissolving organic or inorganic acids in water. The inorganic acids are selected from hydrobromic acid, hydrochloric acid, sulphuric acid, sulfurous acid, nitric acid or phosphoric acid, preferably from hydrochloric acid; the organic acids are selected from methanesulfonic acid, dodecylsulfonic acid, 2-naphthalenesulfonic acid, benzenesulfonic acid, oxalic acid, 2,2-dichloroacetic acid, glycerophosphoric acid, 2-hydroxyethanesulfonic acid, L-aspartic acid, maleic acid, ethanesulfonic acid, 1,5-naphthalenedisulfonic acid, ethane-1,2-disulfonic acid, cyclohexylaminosulfonic acid, or p-toluenesulfonic acid.

In the step of adjusting pH with bases or basic solutions as described in the aforementioned preparation methods 1-4, said bases are organic or inorganic bases, and said basic solutions are solutions as formulated by dissolving organic or inorganic bases in water. Said inorganic bases are selected from potassium hydroxide, sodium hydroxide, zinc hydroxide, calcium hydroxide, potassium carbonate, potassium bicarbonate, sodium carbonate, or sodium bicarbonate, preferably from sodium bicarbonate. Said organic bases are selected from L-arginine, betaine, choline, diethylamine lysine, N,N'-dibenzylethylenediamine,2-(diethylamino)ethanol, 2-aminoethanol, 1-(2-hydroxyethyl)pyrrole, diethanolamine, dimethylethanolamine, N-methylglucamine, tromethamine, triethanolamine, 4-(2-hydroxyethyl)morpholine, imidazole, or ethanediamine.

In the aforementioned preparation method 3, said column chromatography is reverse phase column chromatography, and is selected from $C_4$ column chromatography, $C_8$ column chromatography, $C_{18}$ column chromatography, or resin column chromatography, preferably from $C_{18}$ column chromatography.

The organic solvent in the eluant as described in the aforementioned preparation method 3 and the organic solvent in the mixed solvent as described in the aforementioned preparation method 4 are miscible with water and are selected from lower alcohols containing 1-4 carbon atoms, such as methanol, ethanol, propanol, isopropanol, n-butanol, isobutanol, and the like; lower ketones containing 1-6 carbon atoms, such as acetone, butanone, and the like; acetonitrile; propionitrile or tetrahydrofuran, and the like; preferably from methanol, acetone, and acetonitrile.

In the eluant of the aforementioned preparation method 3, the ratio of organic solvent to water is 1:0.2~1:4, preferably 1:0.5~1:2, most preferably 1:1.

In the aforementioned preparation methods 1-4, said cooling to low temperature refers to cooling to 0~10° C.

The present inventors have conducted a number of studies on the preparation methods of the crystalline form of compound A. The studies shows that after adjusting pH of the aqueous suspension of compound A to reach a homogeneous solution, absorbing and enriching by column chromatography, then eluting with the eluant of organic solvent/water; after eluting, concentrating the eluant by distillation under reduced pressure; after distilling off part of the eluant, the ratio of organic solvent to water in the residual eluant is very essential. If the ratio of organic solvent to water is high, the crystalline form I of compound A will be obtained. If the ratio of organic solvent to water is low, the crystalline form II of the compound will be obtained.

In practice "concentrating the eluant by distillation under reduced pressure until a mixed solvent of organic solvent/water with a certain volume ratio is obtained after concentration", whether the mixed solvent is acetonitrile/water or methanol/water, the eluant will be distilled off together when distilling since both acetonitrile and methanol form azetrope with water. After distilling off part of the eluant under reduced pressure, the ratio of organic solvent to water is difficult to determine quantitatively. Accordingly, the present inventors carried out a series of simulation and verification assays which simulate the ratio of organic solvent to water in the mixed solvent after concentration in order to determine the ratio of organic solvent to water in the concentrated mixed solvent at which the crystalline form I and II can be obtained respectively.

When the mixed solvent is selected from acetonitrile/water and the ratio of acetonitrile to water is 60:40, by adjusted pH, cooling to low temperature, filtering and drying, a crystal is obtained. If the ratio of acetonitrile to water is higher than 60:40, the crystal will not be precipitated. Thus, the upper limit of the ratio of acetonitrile to water is 60:40, i.e. 3:2. (i.e. the content of acetonitrile is 60%). After carrying out a number of assays based on dilution with such ratio, the present inventors conclude that when the ratio of acetonitrile to water in the mixed solvent is no less than 1:9 (i.e. the content of acetonitrile is no less than 10%), the crystalline form as obtained finally is the crystalline form I; when the ratio of acetonitrile to water in the mixed solvent is less than 1:9 (i.e. the content of acetonitrile is less than 10%), the crystalline form as obtained finally is the crystalline form II.

When the mixed solvent is selected from methanol/water and the ratio of methanol to water is 80:20, by adjusting pH, cooling to low temperature, filtering and drying, a crystal is obtained. If the ratio of methanol to water is higher than 80:20, the crystal will not be precipitated. Thus, the upper limit of the ratio of methanol to water is 80:20, i.e. 4:1 (i.e. the content of methanol is 80%). After carrying out a number of assays based on dilution with such ratio, the present inventors conclude that when the ratio of methanol to water in the mixed solvent is no less than 1:4 (i.e. the content of methanol is no less than 20%), the crystalline form as obtained finally is the crystalline form I; when the ratio of methanol to water in the mixed solvent is less than 1:4 (i.e. the content of methanol is less than 20%), the crystalline form as obtained finally is the crystalline form II.

Therefore, the present inventors have determined the ratio of the mixed solvent for obtaining the crystalline form I of compound A, which is 1:9~3:2 for the mixed solvent of acetonitrile/water (i.e. when the content of acetonitrile in the mixed solvent is 10%-60%, the crystalline form I will be obtained), or 1:4~4:1 for the mixed solvent of methanol/water (i.e. when the content of methanol in the mixed solvent is 20%-80%, the crystalline form I will be obtained); and the ratio of the mixed solvent for obtaining the crystalline form II of compound A, which is <1:9 for the mixed solvent of acetonitrile/water (i.e. when the content of acetonitrile in the mixed solvent is <10%, the crystalline form II will be obtained), or <1:4 for the mixed solvent of methanol/water (i.e. when the content of methanol in the mixed solvent is <20%, the crystalline form II will be obtained).

In other words, when the method of column chromatography is used, the eluant is distilled off under reduced pressure to obtain the concentrated mixed solvent of organic solvent/water. At this time, when the volume ratio of acetonitrile/water in the concentrated mixed solvent is 1:9~3:2 (i.e. the content of acetonitrile in the mixed solvent is 10%~60%), or the ratio of methanol/water in the concentrated mixed solvent is 1:4~4:1 (i.e. the content of methanol in the mixed solvent is 20%~80%), the crystalline form I of compound A can be obtained; when the volume ratio of acetonitrile/water in the concentrated mixed solvent is <1:9 (i.e. the content of acetonitrile in the mixed solvent is <10%), or the ratio of methanol/water in the concentrated mixed solvent is <1:4 (i.e. the content of methanol in the mixed solvent is <20%), the crystalline form II of compound A can be obtained. When the method of column chromatography is not used, said "mixed solvent of organic solvent/water" refers to the mixed solvent of acetonitrile/water at a ratio of 1:9~3:2 (i.e. the content of acetonitrile in the mixed solvent is 10%~60%), or the mixed solvent of methanol/water at a ratio of 1:4~4:1 (i.e. the content of methanol in the mixed solvent is 20%~80%), and the crystalline form I of compound A can be obtained at both conditions; the mixed solvent of acetonitrile/water at a ratio of <1:9 (i.e. the content of acetonitrile in the mixed solvent is <10%), or the mixed solvent of methanol/water at a ratio of <1:4 (i.e. the content of methanol in the mixed solvent is <20%), and the crystalline form II of compound A can be obtained at both conditions.

In other words, regarding "concentrated mixed solvent of organic solvent and water" in the aforementioned preparation method 3 or "mixed solvent of organic solvent/water" in the aforementioned preparation method 4, when the organic solvent is acetonitrile, the mixed solvent of acetonitrile/water at a ratio of <1:9 (i.e. the content of acetonitrile in the mixed solvent is <10%), or when the organic solvent is methanol, the mixed solvent of methanol/water at a ratio of <1:4 (i.e. the content of methanol in the mixed solvent is <20%) can result in the crystalline form II of compound A.

In view of the above, when the method of column chromatography is used, most of the organic solvent will be distilled off the eluant when distilling under reduced pressure, and the crystalline form II will be obtained if the ratio of organic solvent in the concentrated mixed solvent as obtained is minor. Therefore, in practical operation, distillation under reduced pressure is stopped when no solvent is obviously distilled off. Measurement shows that the content of organic solvent in the concentrated mixed solvent is minor, and the crystalline form as obtained is the crystalline form II as measured by powder X-ray diffraction.

The crystalline form II as prepared by the above methods is assayed by:

(1) X-ray powder diffraction

Condition for X-ray diffraction assay: Cu-Ka ray, 1.54 Å (monochromator), measured by D/MAX-RB X-ray diffractometer.

The X-ray powder diffraction pattern using Cu-Ka radiation represented as 2θ has strong characteristic peaks at 18.9±0.2, 19.4±0.2, 21.0±0.2, 21.7±0.2, and 23.4±0.2; and has further characteristic peaks at 10.8±0.2, 11.8±0.2, 12.0±0.2, and 23.7±0.2.

When the X-ray diffraction is used for measuring the crystalline form of the present invention, errors should be taken into account as determining the structure of the crystalline form, since the apparatus or condition used for measurement may result in little measurement errors to the peaks measured. Accordingly, the present inventors have considered the error range (±0.2) when determining the 2θ angles.

(2) DSC endothermic assay

Condition for the DSC assay: DZ3335 differential scanning calorimeter, protected by nitrogen gas, at a heating rate of 5° C./min.

The DSC endothermic transition is at 105-117° C., and the highest decomposition temperature is about 170-179° C.

(3) Single crystal diffraction assay

Condition for single crystal diffraction assay: Mo/Kα-beam, Bruker CCD APEX-II single crystal diffractometer The molecular structure pattern of the crystalline form II is obtained by single crystal diffraction, and the cell parameters are as follows:

| Parameters | | Values |
| --- | --- | --- |
| Crystal size | | 0.60 × 0.30 × 0.05 mm |
| Crystal system | | monoclinic |
| Space group | | P 2$_1$ |
| Crystal cell parameters | a (Å) | 9.651(13) |
| | b (Å) | 15.66(2) |
| | c (Å) | 17.13(2) |
| | β (°) | 105.07(3) |
| Crystal cell volume V (Å$^3$) | | 2499(6) |
| Z (number of molecules in a single crystal cell) | | 4 |
| Calculated density (g/cm$^3$) | | 1.46 |
| Diffraction wavelength (Å) | | 0.71073 |

(4) Water content assay

Measured by the Karl Fischer water determination method (refers to the K-F method for short), compound A or hydrate thereof of the present invention has a water content of 6%-10%.

The present invention further provides the use of the crystalline form of compound A or hydrate thereof in the preparation of a medicament for treating and/or preventing infectious diseases.

The present invention also provides a pharmaceutical composition comprising the crystalline form of compound A or hydrate thereof and one or more pharmaceutical carriers and/or diluents, which can be any one of pharmaceutically acceptable dosage forms, such as injections. When formulated as a injection, suitable adjuvants, such as osmotic pressure regulator, pH adjuster, solubilizer, filler, antioxidant, antibacterial agent, emulsifier, suspending agent, and the like can be added according to the properties of the medicament.

BRIEF DESCRIPTION OF THE DRAWINGS

FIG. 1 is the X-ray powder diffraction pattern of the crystalline form II of compound A (prepared by column chromatography using acetonitrile/water as the eluant). The ordinate represents diffraction intensity (CPS), and the abscissa represents diffraction angle (2θ).

FIG. 2 is the X-ray powder diffraction pattern of the crystalline form II of compound A (prepared by column chromatography using acetone/water as the eluant). The ordinate represents diffraction intensity (CPS), and the abscissa represents diffraction angle (2θ).

FIG. 3 is the DSC pattern of the crystalline form II of compound A. The ordinate represents power (mW), and the abscissa represents temperature (° C.).

FIG. 4 is the molecular structure pattern as obtained by the single crystal diffraction of the crystalline form II of compound A.

EXAMPLES

The present invention is further illustrated by the examples in detail hereinafter. The examples are merely illustrative and should not be construed as limitations upon the scope of the present invention. The technical solutions and variants thereof as obtained based on the above disclosure of the present invention fall into the scope of the present invention entirely.

Example 1

Preparation of Amorphous Compound A

In the above synthetic route, -PNZ represents

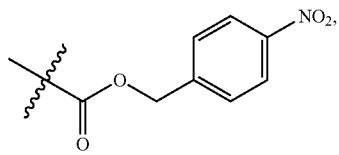 [SMILES: *C(=O)OCc1ccc([N+](=O)[O-])cc1]

-PNB represents

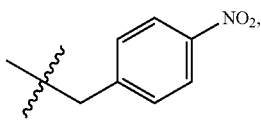 [SMILES: *Cc1ccc([N+](=O)[O-])cc1]

MAP represents

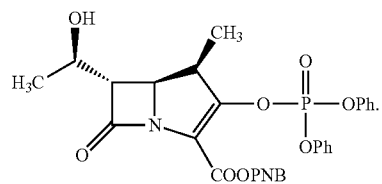

1. Preparative example of intermediate 1

Intermediate 1 is (2S,4S)-4nitrobenzyl 4-mercapto-2-((4-sulfamoylbenzyl)carbamoyl)pyrrolidine-1-carboxylate.

(1S,4S)-4-nitrobenzyl 3-oxo-2-thia-5-azabicylco[2.2.1]heptane-5-carboxylate(raw material 1) (1600 g, 5.19 mol) and mafenide acetate (raw material 2) (1219.2 g, 4.95 mol) were dissolved in acetonitrile, and the solution was warmed to 40° C. Triethylamine was added dropwise under nitrogen

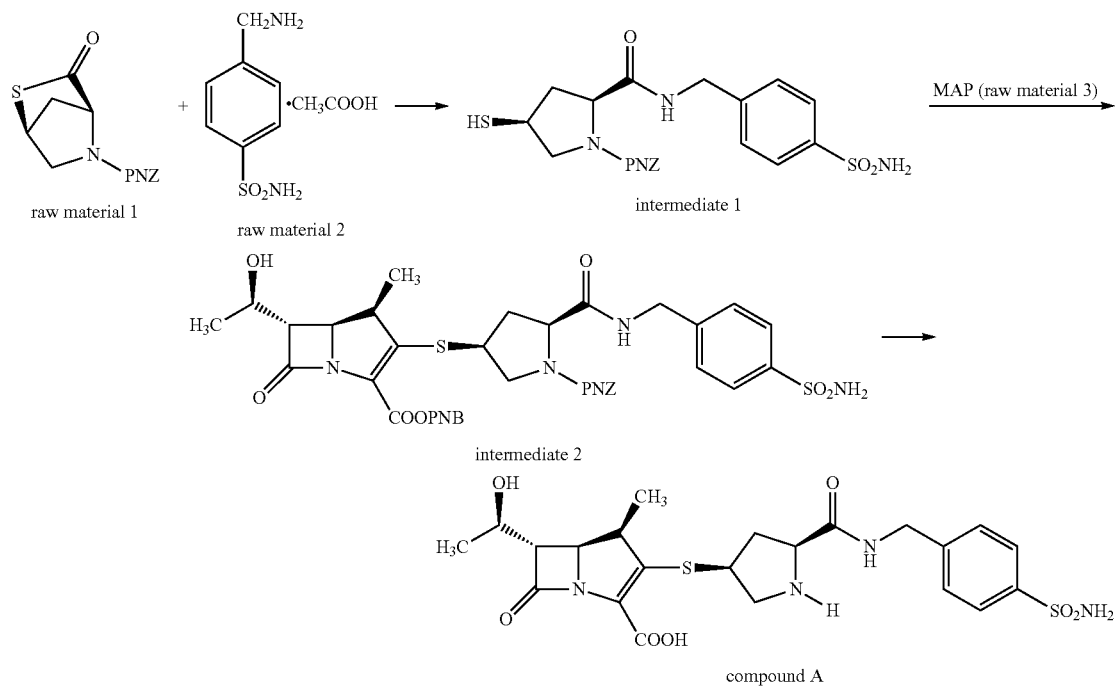

protection, and the reaction mixture was stirred to precipitate, filtered to obtain intermediate 1.

2. Preparative example of intermediate 2

Intermediate 2 is (4R,5S,6S)-4-nitrobenzyl 6-((R)-1-hydroxyethyl)-4-methyl-7-oxo-3-(((3S,5S)-5-((4-sulfamoylbenzyl)carbamoyl)pyrrolidin-3-yl)thio)-1-azabicyclo[3.2.0]hept-2-ene-2-carboxylate.

Intermediate 1 and (4R,5S,6S)-4nitrobenzyl 6-((R)-1-hydroxyethyl)-4-methyl-7-oxo-3-(((3S,5S)-5-((4-sulfamoylbenzyl)carbamoyl)pyrrolidin-3-yl)thio)-1-azabicyclo[3.2.0]hept-2-ene-2-carboxylate (raw material 3) (2980 g, 5.01 mol) were dissolved in dimethylformamide, and the solution was cooled to −15° C. Triethylamine was added dropwise under nitrogen protection. After the reaction is over, ethyl acetate was added. The mixture was sequentially washed with water, dilute hydrochloric acid and saturated sodium bicarbonate, and the organic layer was dried over anhydrous sodium sulfate. The ethyl acetate layer was concentrated and the precipitate was filtered, and dried to obtain 3300 g of a solid (i.e. intermediate 2) with a yield of 79.46% and a purity of 94.75%.

3. Preparative example of compound A

Compound A is (4R,5S,6S)-6-((R)-1-hydroxyethyl)-4-methyl-7-oxo-3-(((3S,5S)-5-((4-sulfamoylbenzyl)carbamoyl)pyrrolidin-3-yl)thio)-1-azabicyclo[3.2.0]hept-2-ene-2-carboxylic acid.

Intermediate 2 (500 g, 0.60 mol) was dissolved in tetrahydrofuran, and sodium bicarbonate (100 g, 1.19 mol) as well as 100.0 g of 10% Pd/C were added into water. The two solutions were placed into hydrogenation reactor and mixed. The hydrogenation reactor was filled with hydrogen gas, pressurized to 4.0 MPa, warmed to 30° C., and stirred until complete reaction. After filtration, the reaction mixture was washed with ethyl acetate. The pH of aqueous layer was adjusted with acetic acid to 6. Subsequently, the mixture was separated by column chromatography with octadecyl bonded silica gel, purified by preparative liquid chromatography, lyophilized to obtain 145.8 g of a solid (i.e. compound A) with a yield of 46.32% and a purity of 96.66%.

Molecular formula: $C_{22}H_{28}N_4O_7S_2$

Molecular weight: 524.6

$^1$H-NMR(D$_2$O, 400 MHz) δ: 1.05 (d, 3H), 1.15 (d, 3H), 1.97 (m, 1H), 2.83 (m, 1H), 3.20 (m, 1H), 3.30 (m, 1H), 3.33 (m, 1H), 3.63 (dd, 1H), 3.92 (m, 1H), 4.08 (m, 1H), 4.10 (m, 1H), 4.40 (dd, 1H), 4.45 (d, 1H), 7.40 (d, 2H), 7.78 (d, 2H).

Example 2

Preparative Example 1 of the Crystalline Form II of Compound A 50 mL of deionized water was added to 2.03 g of compound A, and the resultant mixture was stirred to form a suspension. Then the suspension was adjusted pH with sodium bicarbonate solid until complete dissolution. Afterwards, the solution was enriched with $C_{18}$ column chromatography, and then eluted with a mixed solution of acetonitrile/water at a ratio of 1:1. The eluant was distilled at 30° C. under reduced pressure (at a vacuum degree of 30 mmHg) until no solvent was obviously outflowed, adjusted pH to 6 with 2N hydrochloric acid, and left to rest at 0-5° C. to obtain a crystal, which was filtered, washed with cold water, and dried under vacuum to obtain 1.37 g of the crystalline form II of compound A with a purity of 99.1% and a yield of 67%.

XRD diffraction: the results of XRD diffraction assay are shown in FIG. 1. The crystal has characteristic peaks at the following diffraction angles (2θ): 5.14, 7.50, 10.82, 11.80, 12.10, 13.14, 16.64, 18.88, 19.46, 20.42, 21.08, 21.74, 23.44, 23.76, and 24.52;

DSC decomposition point: the highest decomposition temperature is about 172° C.;

Water content (the K-F method): 7.69%.

Example 3

Preparative Example 2 of the Crystalline Form II of Compound A 50 mL of deionized water was added to 2.01 g of compound A, and the resultant mixture was stirred to form a suspension. Then the suspension was adjusted pH with saturated aqueous sodium bicarbonate solution until complete dissolution. Afterwards, the solution was enriched with $C_{18}$ column chromatography, and then eluted with a mixed solution of acetone/water at a ratio of 1:1. The eluant was distilled at 26° C. under reduced pressure (at a vacuum degree of 30 mmHg) until no solvent was obviously outflowed, adjusted pH to 6 with 2N hydrochloric acid, and left to rest at 0-5° C. to obtain a crystal, which was filtered, washed with cold water, and dried under vacuum to obtain 1.10 g of the crystalline form II of compound A with a purity of 98.8% and a yield of 55%.

XRD diffraction: the results of XRD diffraction assay are shown in FIG. 2. The crystal has characteristic peaks at the following diffraction angles (2θ): 5.14, 10.80, 11.76, 12.08, 16.62, 18.88, 19.42, 20.42, 21.04, 21.70, 23.36, and 23.74;

DSC decomposition point: the highest decomposition temperature is about 172° C.;

Water content (the K-F method): 7.60%.

Example 4

Preparative Example 3 of the Crystalline Form II of Compound A 50 mL of deionized water was added to 2.05 g of compound A, and the resultant mixture was stirred to form a suspension. Then the suspension was adjusted pH with 1N hydrochloric acid until complete dissolution. Afterwards, the solution was enriched with $C_{18}$ column chromatography, and then eluted with a mixed solution of methanol/water at a ratio of 1:1. The eluant was distilled at 30° C. under reduced pressure (at a vacuum degree of 30 mmHg) until no solvent was obviously outflowed, adjusted pH to 6 with saturated aqueous sodium bicarbonate solution, and left to rest at 0-5° C. to obtain a crystal, which was filtered, washed with cold water, and dried under vacuum to obtain 0.92 g of the crystalline form II of compound A with a purity of 98.8% and a yield of 45%.

XRD diffraction: the crystal has characteristic peaks at the following diffraction angles (2θ) in the XRD diffraction pattern: 5.10, 10.76, 11.74, 12.06, 18.90, 19.40, 20.36, 21.02, 21.68, 23.38, 23.70, and 24.48;

DSC decomposition point: the highest decomposition temperature is about 173° C.;

Water content (the K-F method): 7.67%.

Example 5

Preparative Example 4 of the Crystalline Form II of Compound A 50 mL of deionized water was added to 2.08 g of compound A, and the resultant mixture was stirred to form a suspension. Then the suspension was adjusted pH with saturated aqueous sodium bicarbonate solution until complete dissolution. Afterwards, the solution was enriched with $C_{18}$ column chromatography, and then eluted with a mixed solution of methanol/water at a ratio of 1:1. The eluant was distilled at 30° C. under reduced pressure (at a vacuum degree of 30 mmHg) until no solvent was obviously outflowed, adjusted pH to 6 with 2N hydrochloric acid, and left to rest at 0-5° C. to obtain a crystal, which was filtered, washed with cold water, and dried under vacuum to obtain 0.97 g of the crystalline form II of compound A with a purity of 99.0% and a yield of 46.6%.

The cultivation of single crystal is according to the methods of the above examples. The eluant was left to rest for 2 days at 0-10° C. after adjusting pH with 2N hydrochloric acid to obtain a sample suitable for single crystal assay.

XRD diffraction: the crystal has characteristic peaks at the following diffraction angles (2θ) in the XRD diffraction pattern: 10.88, 11.84, 12.16, 18.98, 19.52, 21.12, 21.80, 23.48, and 23.84.

The results of DSC assay: the highest decomposition temperature is about 172° C., the extrapolated initial decomposition temperature is about 163° C., and the results are shown in FIG. 3;

the results of X-ray single crystal diffraction of the single crystal as obtained are shown in FIG. 4, and the single crystal cell parameters are as follows:

| Parameters | | Values |
| --- | --- | --- |
| Crystal size | | 0.60 × 0.30 × 0.05 mm |
| Crystal system | | monoclinic |
| Space group | | P 2$_1$ |
| Crystal cell parameters | a (Å) | 9.651(13) |
| | b (Å) | 15.66(2) |
| | c (Å) | 17.13(2) |
| | β (°) | 105.07(3) |
| Crystal cell volume V (Å$^3$) | | 2499(6) |
| Z (number of molecules in a single crystal cell) | | 4 |
| Calculated density (g/cm$^3$) | | 1.46 |
| Diffraction wavelength (Å) | | 0.71073 |

Water content (the K-F method): 7.57%;

Elemental analysis: in view of $C_{22}H_{28}N_4O_7S_2 \cdot 2H_2O$ calculated: C 47.13%, H 5.75%, and N 9.99%; found: C 47.20%, H 6.06%, and N 10.11%.

Example 6

Preparative Example 5 of the Crystalline Form II of Compound A 20 mL of deionized water was added to 2.02 g of compound A, and the resultant mixture was stirred to obtain a suspension. Then the suspension was adjusted pH with saturated aqueous sodium bicarbonate solution until complete dissolution. Afterwards, the solution was filtered, and the filtrate was adjusted pH to 6 with 2N hydrochloric acid, and left to rest at 0-5° C. to obtain a crystal, which was filtered, washed with cold water, and dried under vacuum to obtain 1.27 g of the crystalline form II of compound A with a purity of 98.0% and a yield of 62.9%.

XRD diffraction: the crystal has characteristic peaks at the following diffraction angles (2θ) in the XRD diffraction pattern: 10.88, 11.86, 12.18, 18.92, 19.52, 21.12, 21.78, 23.50, and 23.80;

DSC decomposition point: the highest decomposition temperature is about 172° C.;

Water content (the K-F method): 7.71%.

Example 7

Preparative Example 6 of the Crystalline Form II of Compound A 20 mL of deionized water was added to 2.0 g of compound A, and 1.25 g of sodium bicarbonate was added at room temperature with stirring to adjust pH until complete dissolution. Afterwards, 0.41 mL of methanol (volume ratio: methanol/water=1:49) was added. The reaction mixture was adjusted pH to 6 with 2N hydrochloric acid solution and stirred to precipitate out a solid, which was filtered, washed with cold water, and dried under vacuum to obtain 1.32 g of the crystalline form II of compound A with a yield of 66.0%.

XRD diffraction: the crystal has characteristic peaks at the following diffraction angles (2θ) in the XRD diffraction pattern: 10.84, 11.80, 12.12, 13.16, 18.88, 19.46, 20.40, 21.06, 21.72, 23.44, 23.70, and 24.52.

Example 8

Preparative Example 7 of the Crystalline Form II of Compound A 5 mL of water was added to 500 mg of compound A, and 0.25 g of sodium bicarbonate was added at room temperature with stirring to adjust pH until complete dissolution. Afterwards, 260 µL of acetonitrile (volume ratio: acetonitrile/water=1:19) was added. The reaction mixture was adjusted pH to 6 with 2N hydrochloric acid solution and stirred to precipitate out a solid, which was filtered, washed with cold water, and dried under vacuum to obtain 350 mg of the crystalline form II of compound A with a yield of 75%.

XRD diffraction: the crystal has characteristic peaks at the following diffraction angles (2θ) in the XRD diffraction pattern: 10.74, 11.68, 12.04, 18.76, 19.32, 20.90, 21.56, 23.30, and 23.56.

Example 9

Stability Assay for the Crystalline Form II of Compound A

The present inventors have investigated the stability of the crystalline form II of compound A as obtained. It can be seen from the results that the crystalline form II of the present invention, as compared with the crystalline form I of compound A as described in CN201010178970.2, has superior stability and has the advantages including high stability and crystallinity, centralized particle size distribution, excellent fluidity of the product, and smooth surface, and the like.

Test compound:

The crystalline form I: prepared by referring to the method of example 1 in CN201010178970.2. The batch number is 20100315-4;

The crystalline form II: prepared by example 2 of the Description. The batch number is 040805.

Test condition: sampled after being placed for 5 and 10 days at a high temperature of 60° C., and the results thus obtained were compared with those obtained at day 0 by measuring water content, related substances and contents thereof. The samples were sealed with plastic bags coated with aluminium foils during the assay.

Water content determination is performed according to the first method (the Karl Fischer method) in Chinese Pharmacopoeia, 2010 edition, Appendix VIII M.

Assay is performed by using the control as the external standard according to the high performance liquid chromatography in Chinese Pharmacopoeia, 2010 edition, Appendix VD.

Operation condition

Apparatus: high performance liquid chromatograph (Agilent 1200 series)

Chromatographic column: Agilent $C_{18}$; filler: 5 μm octadecyl silane boned silica gel; inner diameter: 4.6 mm; length of the column: 150 mm.

Column temperature: 30° C.

Mobile phase: 0.02 M diammonium phosphate (pH=5.2 adjusted by phosphoric acid): acetonitrile=100:7

Flow rate: 1.0 mL/min

Injection volume: 10 μL

Determination of related substances is performed by area normalization method according to the high performance liquid chromatography in Chinese Pharmacopoeia, 2010 edition, Appendix VD.

Operation condition

Apparatus: high performance liquid chromatograph (Agilent 1200 series)

Chromatographic column: Agilent $C_{18}$; filler: 5 μm octadecyl silane boned silica gel; inner diameter: 4.6 mm; length of column: 150 mm.

Column temperature: 30° C.

Mobile phase: A: 0.02 M diammonium phosphate (pH=5.2 adjusted by phosphoric acid): acetonitrile=95:5.

B: 0.02 M diammonium phosphate (pH=5.2 adjusted by phosphoric acid): acetonitrile=30:70.

Gradient condition: see Table 1 below.

TABLE 1

Chromatographic gradient condition for determination of related substances

| T (min) | 0 | 5 | 15 | 18 | 25 | 30 | 35 | 40 | 42 | 47 |
|---|---|---|---|---|---|---|---|---|---|---|
| B% | 0 | 3 | 4 | 15 | 30 | 65 | 100 | 100 | 0 | 0 |

Flow rate: 1.0mL/min
Injection volume: 10 μL

The experimental results as obtained: see Table 2 below.

TABLE 2

Results of stability assay

| Sample name (batch number) | Day | open ring % | Increase open ring % | Total % | Increase total % | Water content % | Decrease in water content % | Content % | Decrease in content % |
|---|---|---|---|---|---|---|---|---|---|
| The crystalline form I (20100315-4) | 0 | 0.136 | — | 1.709 | — | 7.884 | — | 100 | — |
|  | 5 | 0.782 | 0.646 | 2.550 | 0.841 | 7.701 | 0.183 | 96.27 | 3.73 |
|  | 10 | 1.120 | 0.984 | 2.876 | 1.167 | 7.219 | 0.665 | 96.05 | 3.95 |
| The crystalline form II (040805) | 0 | 0.157 | — | 1.046 | — | 8.316 | — | 100 | — |
|  | 5 | 0.789 | 0.632 | 1.573 | 0.527 | 8.290 | 0.026 | 98.43 | 1.57 |
|  | 10 | 1.101 | 0.944 | 1.899 | 0.853 | 7.914 | 0.402 | 97.76 | 2.24 |

Note:
Compound A is easily hydrolyzed. After hydrolysis, the β-lactam ring is opened, which results in the main impurity briefly called the open ring product, and the content of the open ring product is considered as a factor for stability determination.
In table 2, open ring % refers to the content of open ring product; total % refers to the total content of related substances; increase open ring % refers to the increased amount of the open ring product placed for 5 and 10 days at a high temperature of 60° C. as compared with the amount at day 0;
increase total % refers to the increased amount of total related substances placed for 5 and 10 days at a high temperature of 60° C. as compared with the amount at day 0.

The open-ring product:

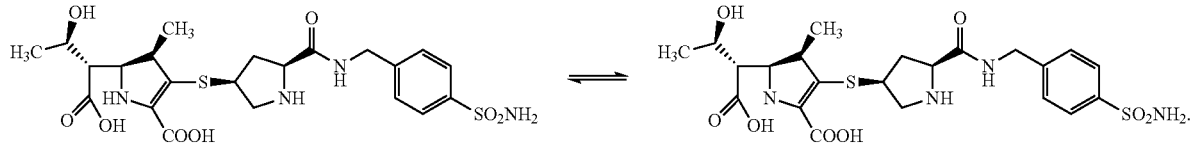 [SMILES: C[C@@H](O)[C@@H](C(=O)O)[C@@H]1NC(C(=O)O)=C(S[C@@H]2CN[C@H](C(=O)NCc3ccc(S(N)(=O)=O)cc3)C2)[C@@H]1C ; C[C@@H](O)[C@@H](C(=O)O)[C@@H]1NC(C(=O)O)=C(S[C@@H]2CN[C@H](C(=O)NCc3ccc(S(N)(=O)=O)cc3)C2)[C@@H]1C]

It can be seen from Table 2 that after being placed for 5 and 10 days at a high temperature of 60° C., the increased amount of the open ring product of the crystalline form II is lower than that of the crystalline form I; the increased amount of the content of total impurities of the crystalline form II is lower than that of the crystalline form I; the decreased amount of the water content of the crystalline form II is lower than that of the crystalline form I; the decreased amount of the content of crystalline form II is lower than that of the crystalline form I. Accordingly, as compared with the crystalline form I, the increase in the content of impurities, the decrease in the water content, and the decrease in the content of the crystalline form II is lower, such that the crystalline form II surpasses the crystalline form I in each aspect of properties, which shows that the stability of the crystalline form II of compound A is better than that of the crystalline form I.

Example 10

Preparative Example of the Injection of the Crystalline Form II of Compound A

1. Formula:
The crystalline form II of 250 g (calculated as $C_{22}H_{28}N_4O_7S_2$) compound A Anhydrous sodium carbonate 50 g
Totally prepared 1000 bottles 2. Procedure:
(1) The antibiotic glass bottles and rubber plugs used for the preparation were washed, dried and sterilized;
(2) the air-condition and dehumidification equipment were turned on, controlling the inside relative humidity of the grade 100 laminar flow room within 50%;
(3) the crystalline form II of compound A and anhydrous sodium carbonate were weighed according to the formula, and were uniformly mixed to obtain a sterile mixed powder;
(4) the semifinished products were measured;
(5) separately loaded;
(6) plugs were added;
(7) capped;
(8) the finished products were generally inspected;
(9) packed and warehoused.

Example 11

Antibacterial Activity Assay of the Crystalline Form II of Compound A

Test strains: the following clinically isolated strains were provided by public organizations.
Gram-positive bacteria: methicillin sensitive *Staphylococcus aureus* (MSSA), and penicillin sensitive *Streptococcus pneumoniae;*
Gram-negative bacteria: ESBLs negative *Escherichia coli*, ESBLs positive *Escherichia coli, Haemophilus influenzae*, and Moraxelle catarrhalis.

Test compound: the crystalline form II of compound A
Experimental method: standard agar double dilution method was adopted.
Experimental Results and Conclusions:

Antibacterial Activity of the Crystalline Form II of Compound A Against Clinically Isolated Strains

| Strains | $MIC_{mode}$ (mg/L) | $MIC_{90}$ (mg/L) |
|---|---|---|
| MSSA | 0.062 | 0.062 |
| Penicillin sensitive *Streptococcus pneumoniae* | 0.008 | 0.031 |
| ESBLs negative *Escherichia coli* | 0.016 | 0.016 |
| ESBLs positive *Escherichia coli* | 0.016 | 0.25 |
| *Haemophilus influenzae* | 0.062 | 0.125 |
| *Moraxelle catarrhalis* | 0.004 | 0.008 |

The above experimental results indicate that the crystalline form II of compound A exhibits excellent antibacterial activity against both Gram-positive and Gram-negative bacteria, and has a broad antibacterial spectrum and a superior potential for clinical application.

The present invention is described and illustrated in detail hereinbefore; however, the scope thereof is not confined to it. All the modifications, amendments, improvements and changes to the technical solutions of the present invention are within the spirit and scope of the present invention as defined by the appended claims.

What we claim:
1. The crystalline form of carbapenem derivative (4R,5S,6S)-6-((R)-1-hydroxyethyl)-4-methyl-7-oxo-3-(((3S,5S)-5-((4-sulfamoylbenzyl)carbamoyl)pyrrolidin-3-yl)thio)-1-azabicyclo[3.2.0]hept-2-ene-2-carboxylic acid as represented by formula (I) or hydrate thereof, characterized in that the X-ray powder diffraction pattern thereof using Cu-Kα radiation represented as 2θ has characteristic peaks at 18.9±0.2, 19.4±0.2, 21.0±0.2, 21.7±0.2, and 23.4±0.2,

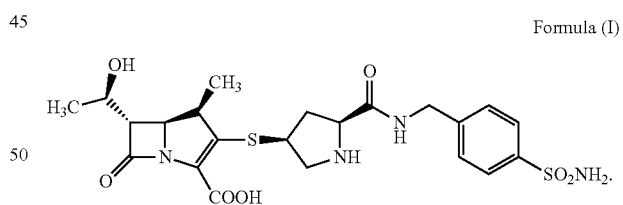

Formula (I)

2. The crystalline form of claim 1, characterized in that the X-ray powder diffraction pattern using Cu-Kα radiation represented as 2θ has further characteristic peaks at 10.8±0.2, 11.8±0.2, 12.0±0.2, and 23.7±0.2.
3. The crystalline form of claim 1 or 2, characterized in that the differential scanning calorimetry (DSC) endothermic transition of said crystalline form is between 105-117° C., and the highest decomposition temperature of said crystalline form is 170-179° C.
4. The crystalline form of claim 1 or 2, characterized in that the water content thereof is 6%-10%.
5. A method for preparing the crystalline form of carbapenem derivative (4R,5S,6S)-6-((R)-1-hydroxyethyl)-4-methyl-7-oxo-3-(((3S,5S)-5-((4-sulfamoylbenzyl)carbamoyl)

pyrrolidin-3-yl)thio)-1-azabicyclo[3.2.0]hept-2-ene-2-carboxylic acid or hydrate thereof of claim 1, characterized in that: after adding bases or basic solutions to an aqueous suspension of (4R,5S,6S)-6-((R)-1-hydroxyethyl)-4-methyl-7-oxo-3-(((3S,5S)-5-((4-sulfamoylbenzyl)carbamoyl)pyrrolidin-3-yl)thio)-1-azabicyclo[3.2.0]hept-2-ene-2-carboxylic acid to adjust pH until complete dissolution, adjusting pH to 5.4-7.0 with acids or acidic solutions, cooling to a temperature between 0 to 10° C., filtering and drying to obtain a crystal.

6. A method for preparing the crystalline form of carbapenem derivative (4R,5S,6S)-6-((R)-1-hydroxyethyl)-4-methyl-7-oxo-3-(((3S,5S)-5-((4-sulfamoylbenzyl)carbamoyl)pyrrolidin-3-yl)thio)-1-azabicyclo[3.2.0]hept-2-ene-2-carboxylic acid or hydrate thereof of claim 1, characterized in that: after adding acids or acidic solutions to an aqueous suspension of (4R,5S,6S)-6-((R)-1-hydroxyethyl)-4-methyl-7-oxo-3-(((3S,5S)-5-(4-sulfamoylbenzyl)carbamoyl)pyrrolidin-3-yl)thio)-1-azabicyclo[3.2.0]hept-2-ene-2-carboxylic acid to adjust pH until complete dissolution, adjusting pH to 5.4-7.0 with bases or basic solutions, cooling to a temperature between 0 and 10° C., filtering and drying to obtain a crystal.

7. A method for preparing the crystalline form of carbapenem derivative (4R,5S,6S)-6-((R)-1-hydroxyethyl)-4-methyl-7-oxo-3-(((3S,5S)-5-((4-sulfamoylbenzyl)carbamoyl)pyrrolidin-3-yl)thio)-1-azabicyclo[3.2.0]hept-2-ene-2-carboxylic acid or hydrate thereof of claim 1, characterized in that: formulating (4R,5S,6S)-6-((R)-1-hydroxyethyl)-4-methyl-7-oxo-3-(((3S,5S)-5-((4-sulfamoylbenzyl)carbamoyl)pyrrolidin-3-yl)thio)-1-azabicyclo[3.2.0]hept-2-ene-2-carboxylic acid as an aqueous suspension; after adjusting pH until complete dissolution, absorbing and enriching the solution by column chromatography, then eluting with an eluant of organic solvent/water; distilling the eluant off under reduced pressure to obtain a concentrated mixed solvent of organic solvent/water; adjusting pH to 5.4-7.0, cooling to a temperature between 0 and 10° C., filtering and drying to obtain a crystal.

8. A method for preparing the crystalline form of carbapenem derivative (4R,5S,6S)-6-((R)-1-hydroxyethyl)-4-methyl-7-oxo-3-(((3S,5S)-5-(4-sulfamoylbenzyl)carbamoyl)pyrrolidin-3-yl)thio)-1-azabicyclo[3.2.0]hept-2-ene-2-carboxylic acid or hydrate thereof of claim 1, characterized in that: formulating (4R,5S,6S)-6-((R)-1-hydroxyethyl)-4-methyl-7-oxo-3-(((3S,5S)-5-((4-sulfamoylbenzyl)carbamoyl)pyrrolidin-3-yl)thio)-1-azabicyclo[3.2.0]hept-2-ene-2-carboxylic acid as an aqueous suspension; after adjusting pH until complete dissolution, adding a mixed solvent of organic solvent/water; adjusting pH to 5.4-7.0, cooling to a temperature between 0 and 10° C., filtering and drying to obtain a crystal.

9. The method of claim 7 or 8, characterized in that: adjusting pH with acids, acidic solutions, bases or basic solutions.

10. The method of claim 5 or 6, characterized in that said acids are inorganic or organic acids, and said acidic solutions are solutions as formulated by dissolving organic or inorganic acids in water, wherein the inorganic acids are selected from hydrobromic acid, hydrochloric acid, sulphuric acid, sulfurous acid, nitric acid or phosphoric acid; the organic acids are selected from methanesulfonic acid, dodecylsulfonic acid, 2-naphthalenesulfonic acid, benzenesulfonic acid, oxalic acid, 2,2-dichloroacetic acid, glycerophosphoric acid, 2-hydroxyethanesulfonic acid, L-aspartic acid, maleic acid, ethanesulfonic acid, 1,5-naphthalenedisulfonic acid, ethane-1,2-disulfonic acid, cyclohexylaminosulfonic acid, or p-toluenesulfonic acid; said bases are organic or inorganic bases, and said basic solutions are solutions as formulated by dissolving organic or inorganic bases in water, wherein said inorganic base are selected from potassium hydroxide, sodium hydroxide, zinc hydroxide, calcium hydroxide, potassium carbonate, potassium bicarbonate, sodium carbonate, or sodium bicarbonate; said organic bases are selected from L-arginine, betaine, choline, diethylamine, lysine, N,N'-dibenzylethylenediamine, 2-(diethylamino)ethanol, 2-aminoethanol, 1-(2-hydroxyethyl)pyrrole, diethanolamine, dimethylethanolamine, N-methylglucamine, tromethamine, triethanolamine, 4-(2-hydroxyethyl)morpholine, imidazole, or ethanediamine.

11. The method of claim 7, wherein said column chromatography is reverse phase column chromatography, and is selected from $C_4$ column chromatography, $C_8$ column chromatography, $C_{18}$ column chromatography, or resin column chromatography.

12. The method of claim 7 or 8, wherein the organic solvent in the eluant or the mixed solvent is an organic solvent miscible with water and is selected from lower alcohols containing 1-4 carbon atoms, lower ketones containing 1-6 carbon atoms, acetonitrile, propionitrile or tetrahydrofuran.

13. The method of claim 7, wherein the ratio of organic solvent to water in the eluant is 1:0.2-1:4.

14. The method of claim 7, wherein the ratio of organic solvent to water in the eluent is 1:0.5-1:2.

15. The method of claim 7, wherein the ratio of organic solvent to water in the eluent is 1:1.

16. The method of claim 7 or 8, wherein: when the organic solvent is acetonitrile, the ratio of organic solvent to water in the mixed solvent of organic solvent/water is <1:9; when the organic solvent is methanol, the ratio of organic solvent to water in the mixed solvent of organic solvent/water is <1:4.

17. A method for treating an infectious disease, comprising administering the crystalline form of claim 1 or 2 to a subject in need thereof.

18. A pharmaceutical composition comprising the crystalline form of claim 1 or 2 and one or more pharmaceutical carriers and/or diluents, which can be any one of pharmaceutical acceptable dosage forms.

19. The pharmaceutical composition of claim 18, wherein said dosage forms are injections.

20. The method of claim 9, characterized in that said acids are inorganic or organic acids, and said acidic solutions are solutions as formulated by dissolving organic or inorganic acids in water, wherein the inorganic acids are selected from hydrobromic acid, hydrochloric acid, sulphuric acid, sulfurous acid, nitric acid or phosphoric acid; the organic acids are selected from methanesulfonic acid, dodecylsulfonic acid, 2-naphthalenesulfonic acid, benzenesulfonic acid, oxalic acid, 2,2-dichloroacetic acid, glycerophosphoric acid, 2-hydroxyethanesulfonic acid, L-aspartic acid, maleic acid, ethanesulfonic acid, 1,5-naphthalenedisulfonic acid, ethane-1,2-disulfonic acid, cyclohexylaminosulfonic acid, or p-toluenesulfonic acid; said bases are organic or inorganic bases, and said basic solutions are solutions as formulated by dissolving organic or inorganic bases in water, wherein said inorganic base are selected from potassium hydroxide, sodium hydroxide, zinc hydroxide, calcium hydroxide, potassium carbonate, potassium bicarbonate, sodium carbonate, or sodium bicarbonate; said organic bases are selected from L-arginine, betaine, choline, diethylamine, lysine, N,N'-dibenzylethylenediamine, 2-(diethylamino)ethanol, 2-aminoethanol, 1-(2-hydroxyethyl)pyrrole, diethanolamine, dimethylethanolamine, N-methylglucamine, tromethamine, triethanolamine, 4-(2-hydroxyethyl)morpholine, imidazole, or ethanediamine.

* * * * *

UNITED STATES PATENT AND TRADEMARK OFFICE
CERTIFICATE OF CORRECTION

PATENT NO. : 8,822,445 B2  
APPLICATION NO. : 13/701704  
DATED : September 2, 2014  
INVENTOR(S) : Zhenhua Huang and Yanyan Dong Page 1 of 1

It is certified that error appears in the above-identified patent and that said Letters Patent is hereby corrected as shown below:

In the Claims,

Column 17, Claim 6, Line 18, replace "7-oxo-3-(((3S, 5S)-5-(4-sulfamoylbenzyl)" with --7-oxo-3-(((3S, 5S)-5-((4-sulfamoylbenzyl)--.

Column 17, Claim 8, Line 41, replace "7-oxo-3-(((3S, 5S)-5-(4-sulfamoylbenzyl)" with --7-oxo-3-(((3S, 5S)-5-((4-sulfamoylbenzyl)--.

Signed and Sealed this
Eighth Day of September, 2015

Michelle K. Lee
*Director of the United States Patent and Trademark Office*